United States Patent
Garcia-Rodenas et al.

(10) Patent No.: US 6,733,770 B1
(45) Date of Patent: May 11, 2004

(54) NUTRITIONAL COMPOSITION INTENDED FOR SPECIFIC GASTRO-INTESTINAL MATURATION IN PREMATURE MAMMALS

(75) Inventors: Clara L. Garcia-Rodenas, Forel (CH); Paul-Andre Finot, St. Legier-La Chisaz (CH); Jean-Claude Maire, Belmont/Lausanne (CH); Olivier Ballevre, Lausanne (CH); Anne Net-Hughes, Saint-Legier (CH); Ferdinand Haschke, Lutry (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/936,446

(22) PCT Filed: Mar. 1, 2000

(86) PCT No.: PCT/EP00/01744

§ 371 (c)(1), (2), (4) Date: Mar. 4, 2002

(87) PCT Pub. No.: WO00/54603

PCT Pub. Date: Sep. 21, 2000

(30) Foreign Application Priority Data

Mar. 12, 1999 (EP) ............................................. 99200753

(51) Int. Cl.[7] ........................ A61K 47/00; A61K 38/00; A01N 37/18
(52) U.S. Cl. ............................................. 424/439; 514/2
(58) Field of Search ................................ 424/439; 514/2

(56) References Cited

U.S. PATENT DOCUMENTS 4,977,137 A * 12/1990 Nichols et al.
5,183,805 A * 2/1993 Lee et al.
5,514,655 A * 5/1996 Dewille et al.

FOREIGN PATENT DOCUMENTS

| CA | 2163379 | 5/1996 |
| EP | 0 322 589 | 7/1989 |
| EP | 0 631 731 | 1/1995 |
| EP | 0 827 697 | 3/1998 |
| EP | 0 852 913 | 7/1998 |

OTHER PUBLICATIONS

Hamosh, Margit; "Symposium: Bioactive Components in Milk and Development of the Neonate: Does Their Absence Make a Difference?"; American Society for Nutritional Sciences J. Nutr.; vol. 127; 1997; pp971S–974S.

Schanbacher, F.L. et al.; "Milk–Borne Bioactive Peptides"; Dep. of Animal Sci., Lab. of Molecular & Dev. Biol., Ohio Agric. Res. & Dev. Cent., Ohio State University; 1998; pp 393–403.

* cited by examiner

*Primary Examiner*—Chris Tate
*Assistant Examiner*—Randall Winston
(74) *Attorney, Agent, or Firm*—Bell, Boyd & Lloyd LLC

(57) ABSTRACT

A nutritional enteral composition intended for favoring the growth and maturation of non-mature gastro-intestinal tracts of young mammals, which contains as a protein source a mixture of dietary protein hydrolysates and intact proteins being partly in the form of bioactive peptides.

24 Claims, No Drawings

NUTRITIONAL COMPOSITION INTENDED FOR SPECIFIC GASTRO-INTESTINAL MATURATION IN PREMATURE MAMMALS

FIELD OF THE INVENTION

This invention relates to an enteral composition containing peptides in an adapted profile size, bioactive peptides, intact proteins, and free amino acids intended for specific gastro-intestinal maturation in premature mammals.

BACKGROUND TO THE INVENTION

Nutritional compositions based upon hydrolysates of proteins such as milk or soy, are commonly used in infant and clinical nutrition and particularly in hypoallergenic formulas and, formulas for patients suffering from various intestinal absorption problems. It is also known to use free amino acids in nutritional compositions for example for patients suffering from particular diseases or conditions such as inflammatory bowel disease, intractable diarrhoea, short bowel syndrome, and the like. Accordingly, amino acids are used either alone or in combination with protein or protein hydrolysates. Protein hydrolysates or free amino acid mixtures are also mainly used in, particular cases such as allergy to whole proteins.

Another interest in using protein hydrolysates in nutrition is due to the fact that they are more rapidly absorbed in the intestine than whole protein or free amino acids. However, it is not clear whether this faster absorption translates into better nitrogen utilisation since studies carried out to date have provided conflicting results (Collin-Vidal et al; 1994; Endocrinol. Metab., 30, E 907-914). Further, this interest is in the sense of providing a source of amino acids to meet the general amino acids needs of the patient and not to specifically provide for the needs of individual gastro-intestinal maturation.

SUMMARY OF THE INVENTION

Accordingly, on one aspect, this invention provides a nutritional enteral composition intended for favoring the growth and maturation of non-mature gastro-intestinal tracts of young mammals, which contains as a protein source a mixture of dietary protein hydrolysates and intact proteins being partly in the form of bioactive peptides.

In this composition, the dietary protein hydrolysates are preferably in the form of a mixture of different size peptides, free amino acids or a mixture thereof. The dietary protein hydrolysates may be hydrolysates of animal proteins (such as milk proteins, meat proteins and egg proteins), or vegetable proteins (such as soy proteins, wheat proteins, rice proteins, and pea proteins). The preferred source is milk protein. The dietary protein hydrolysates can be used as such or like peptide fractions isolated from them.

The hydrolysed proteins may comprise at least 5% (by weight, of the total protein content calculated as Nitrogen× 6.25) of hydrolysate having a degree of hydrolysis of about 40 and at least 5% of hydrolysates having a lesser degree of hydrolysis. Free amino acids are preferably in an amount of about 0 to 20% by weight of the total protein content (N×6.25).

The intact proteins may be individual or enriched animal or vegetable protein fractions comprising whole milk, caseins, whey proteins, soy proteins or rice proteins, for example. They are preferably in an amount of at least about 5% of the total protein content N×6.25).

The intact protein fraction may contain bioactive peptides such as TGF-β2 or a source of bioactive peptides such as beta-casein liberated in the gut by enzymatic hydrolysis. The final TGF-β2 concentration may be in the range of 0.1 to 4 ng/mg total protein, preferably about 1 to 2.5 ng/mg.

The nutritional composition may also contain a source of fat and a source of carbohydrates. This composition preferably contains a source of protein providing 5 to 30% of the total energy, a source of carbohydrates which provides 40 to 80% of the total energy, a source of lipids which provides 5 to 55% of the total energy, minerals and vitamins to meet daily requirements.

In another aspect, this invention provides the use of a selected mixture of dietary protein hydrolysates and intact proteins being partly in the form of bioactive peptides for the preparation of a nutritional enteral composition for favoring the growth and maturation of non- or premature gastro-intestinal tracts of young mammals.

The nutritional composition also intends to cover very high nutrient needs for growth and development during that stage. It ensures optimal digestion and utilization (for tissue accretion) of the protein source and intends to minimize the nitrogen waste of the organism. Moreover, a mixture of intact protein, protein hydrolysates, bioactive peptides and free amino acids provides a better source of amino acids to meet the general amino acid needs of the patient in addition to specifically favor the maturation of individual organs.

Embodiments of the invention are now described by way of example only.

DETAILED DESCRIPTION OF THE INVENTION

In the specification, the term "degree of hydrolysis" (DH) means the percentage of nitrogen in the form of free alpha-amino nitrogen as compared to total nitrogen. It is a measure of the extent to which the protein has been hydrolysed.

The term bioactive peptide relates to i) a protein or peptide present as such in the preparation and demonstrating specific fictional properties or ii) a protein or peptide containing an amino acid sequence with specific properties, this sequence being liberated in the gastro-intestinal tract during the natural process of digestion.

According to a first aspect of the invention, the nutritional composition comprises as a source of protein a selected mixture of intact protein being partly in the form of bioactive peptides and dietary protein hydrolysates having a degree of hydrolysis in the range of about 5% to about 50% and free amino acids. The non-protein nitrogen concentration of the protein source can be comprised between 10% and 95% of the total nitrogen. Such protein source maximizes the area of the intestine in which the protein is digested and optimizes protein synthesis in the gut and peripheral tissues.

The nutritional composition can also contain a carbohydrate sources a fat source, vitamins and minerals.

The intact protein may be any suitable dietary protein; for example animal proteins (such as milk proteins, meat proteins and egg proteins); vegetable proteins (such as soy protein, wheat protein, rice protein, and pea protein); or combinations thereof. Milk proteins such as cased and whey protein are particularly preferred. They are preferably in an amount at least of about 5% of the total protein content (calculated as Nitrogen×6.25). Dietary protein in the form of intact protein is found to increase the rate of muscle protein synthesis as compared to protein hydrolysates.

The dietary protein hydrolysates may come from any suitable dietary protein; for example animal proteins (such as milk proteins, meat proteins and egg proteins); vegetable proteins (such as soy protein, wheat protein, rice protein, and pea protein); or combinations thereof. Milk proteins such as casein and whey protein are particularly preferred. The hydrolysed dietary proteins may comprise at least 5% (by weight, of the total protein content calculated as Nitrogen× 6.25) of hydrolysate having a degree of hydrolysis of about 40 and at least 5% of hydrolysates having a lesser degree of hydrolysis. In particular, hydrolysates having a degree of hydrolysis of about 10% to about 15%, are found to increase relative weight of the liver as compared to free amino acid mixes. Hydrolysates having a degree of hydrolysis of about 15% to about 25% are found to increase the concentration of protein in the jejunum, the relative weight of the jejunum and the rate of protein synthesis in the jejunum. Highly hydrolysed protein which has a degree of hydrolysis of greater than 25% or which contains more than 25% by weight of di- and tri-peptides, more preferably greater than 30%, is found to increase the rate of protein synthesis in the jejunum and the duodenum; particularly the duodenum.

The diet, protein hydrolysates may be produced using procedures which are well known in the art or may be obtained commercially. For example, nutritional formulas containing hydrolysates having a degree of hydrolysis less than about 15% are commercially available from Nestlé Nutrition Company under the trade mark Peptamen®. Hydrolysates having a degree of hydrolysis above about 15% may be prepared using the procedure described in EP 0322589.

The dietary protein hydrolysate source may also be in the form of a mix of free amino acids; preferably such that the mix provides a balanced amino acid profile. Free amino acids are preferably in an amount of about 0 to 20% by weight of the total protein content (calculated as Nitrogen× 6.25). Dietary protein in the form of a mix of free amino acids is found to increase the relative weight of the jejunum and the rate of protein synthesis in the jejunum.

The source of total proteins preferably provides about 5% to about 30% of the energy of the nutritional composition; for example about 10% to about 20% of the energy. The remaining energy of the nutritional composition may be provided in the form of carbohydrates and fats.

If the nutritional, composition includes a fat source, the fat source preferably provides about 5% to about 55% of the energy of the nutritional composition; for example about 20% to about 50% of the energy. The lipids making up the fat source may be any suitable fat or fat mixture. Vegetable fats are particularly suitable; for example soy oil, palm oil, coconut oil, safflower oil, sunflower oil, corn oil, canola oil, lecithins, and the like. Animal fats such as milk fats may also be added if desired. The lipids may also include medium-chain triglycerides; for example up to about 60% by weight of lipids as medium-chain triglycerides. Fractionated coconut oil is a suitable source of medium-chain triglycerides.

A source of carbohydrate may be added to the nutritional composition. It preferably provides, about 40% to about 80% of the energy of the nutritional composition. Any suitable carbohydrates may be used, for example sucrose, lactose, glucose, fructose, corn syrup solids, and maltodextrins, and mixtures thereof.

Dietary fibre may also be added if desired. If used, it preferably comprises up to about 5% of the energy of the nutritional composition. The dietary fibre may be from any suitable origin, including for example soy, pea, oat, pectin, guar gum, and gum arabic.

Suitable vitamins and minerals may be included in the nutritional composition in an amount to meet the appropriate guidelines.

One or more food grade emulsifiers may be incorporated into the nutritional composition if desired; for example diacetyl tartaric acid esters of mono-diglycerides, lecithin and mono- and di-glycerides. Similarly suitable salts and stabilisers may be included.

The nutritional composition is preferably enterally administrable; for example in the form of a powder, a liquid concentrate, a ready-to-drink, or a ready-to-administer beverage.

The nutritional composition may be prepared in any suitable manner. For example, it may be prepared by blending together the source of dietary protein, the carbohydrate source, and the fat source in appropriate proportions. If used, the emulsifiers may be included in the blend. The vitamins and minerals may be added at this point but are usually added later to avoid thermal degradation. Any lipophilic vitamins, emulsifiers and the like may be dissolved into: the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used: to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger, for example a plate heat exchanger.

Then, the liquid mixture may be cooled to about 60° C. to about: 85° C.; for example by flash cooling. The liquid mixture may then be again homogenised; for example in two stages at about 7 MPa to about 40 MPa in the first stage and about 2 MPa to about 14 MPa in the second stage. The homogenised mixture may then be further cooled to add any heat sensitive components; such as vitamins and minerals. The pH and solids content of the homogenised mixture is conveniently standardised at this point.

If it is desired to produce a powdered nutritional composition, the homogenised mixture is transferred to a suitable drying apparatus such as a spray drier or freeze drier and converted to powder. The powder should have a moisture content of less than about 5% by weight.

If it is desired to produce a liquid composition, the homogenised mixture is preferably aseptically filled into suitable containers by pre-heating the homogenised mixture (for example to about 75 to 85° C.) and then injecting steam into the homogenised mixture to raise the temperature to about 140 to 160+ C.; for example at about 150° C. The homogenised mixture may then be cooled, for example by flash cooling, to a temperature of about 75 to 85° C. The homogenised mixture may then be homogenised, further cooled to about room temperature and filled into containers. Suitable apparatus for carrying out aseptic filling of this nature is commercially available. The liquid composition may be in the form of a ready to feed composition having a solids content of about 10 to about 14% by weight or may be in the form of a concentrate; usually of solids content of about 20 to about 26% by weight. Flavours may be added to the liquid compositions so that the compositions are provided in the form of convenient, flavoursome, ready-to-drink beverages.

In another aspect, this invention provides a method for increasing protein concentration and synthesis in the small intestine, the method comprising administering to a premature or non-mature mammal an effective amount of a nutritional composition containing a dietary protein hydrolysates having a degree of hydrolysis of less than 50% and intact proteins being partly in the form of bioactive peptides. Further, the dietary protein hydrolysate preferably has a non-protein nitrogen concentration of at least about 85% of total nitrogen. Non protein nitrogen is defined as the nitrogen fraction not recovered as a precipitate after acidification.

Preferably, the method may be used to treat premature or non-mature young mammals to promote growth and maturation of the gastro-intestinal tract. Additionally, the method can also apply to situations encountered in clinical nutrition when alterations of the normal growth or turnover of the gut mucosa occur, e.g. after long term total parenteral nutrition or malnutrition.

The nutritional enteral composition also intends to cover very high nutrient needs for growth, development and maintenance during those situations. It ensures optimal digestion and utilization (for tissue accretion) of the protein source and intends to minimize the nitrogen waste of the organism. The composition may also be used for patients with gut mucosa dammage.

The amount of the nutritional composition to be administered will vary depending upon the state of maturation or growth of the gut of the mammal.

EXAMPLE 1

Whole Protein

An amount of 5 kg of whey protein (obtained from Meggle GmbH under the trade, name Globulal 80) is dispersed in demineralised water at 55° C. to obtain protein concentration (N*6.38) of 10% by weight. The pH of the dispersion is adjusted by the addition of 190 g of calcium hydroxide and the dispersion is cooled to room temperature. The proteins are then dried by lyophilisation and packaged into metal cans.

The whole proteins have a degree of hydrolysis of about 4.41% and a non protein nitrogen concentration of about 1.1% on the basis of total nitrogen.

Hydrolysate 1

An amount of 6.25 kg of whey protein (obtained from Meggle GmbH) is dispersed in 50 liters of demineralised water at 55° C. The pH of the dispersion is adjusted to 8.2 by the addition of 1.8 liters of 2M $Ca(OH)_2$. The proteins are then hydrolysed using 30 g of trypsin (Salt free pancreatic trypsin which has an activity of 6.8 AU/g and a chymotrypsin content of less than 5% and which is obtainable from Novo Nordisk Ferment AG, Dittigen, Switzerland). The hydrolysis reaction is continued for 4 hours at 55° C. During the reaction, the pH is regulated to 7.4 by the addition of 1.6N NaOH and 0.4N KOH. The enzymes are then inactivated by heating the reaction mixture to 80° C. and holding, the mixture at this temperature for about 5 minutes. The mixture is then cooled to 16° C. The hydrolysed proteins are then dried by lyophilisation and packaged into metal cans. The hydrolysate has a degree of hydrolysis of about 14% and a non protein nitrogen concentration of about 54.5% on the basis of total nitrogen.

Hydrolysate 2

An amount of 6.25 kg of whey protein (obtained from Meggle GmbH) is dispersed in 50 liters of demineralised water at 55° C. The pH of the dispersion is adjusted to 7.5 by the addition of 1.6 liters of 1M $Ca(OH)_2$ and 162 ml of a solution of 1.6M NaOH and 0.4M KOH. The proteins are then hydrolysed using 50 g of trypsin (obtainable from Novo Nordisk Ferment AG). The hydrolysis reaction is continued for 4 hours at 55° C. During the reaction, the pH is regulated to 7.4 by the addition of 1.6N NaOH and 0.4N KOH. The enzymes are then inactivated and non-hydrolysed protein is denatured, by heating the reaction mixture to 90° C. and holding the mixture at this temperature for about 5 minutes.

The mixture is then cooled to 56° C. and hydrolysed again for 1 hour using 50 g of trypsin at 55° C. During the reaction, the pH is regulated to 7.4 by the addition of 1.6N NaOH and 0.4N KOH. The enzymes are then inactivated by heating the reaction mixture to 80° C. and holding the mixture at this temperature for about 5 minutes. The mixture is then cooled to 18° C. The hydrolysed proteins are then dried by lyophilisation and packaged into metal cans.

The hydrolysate has a degree of hydrolysis of about 17.3% and a non protein nitrogen concentration of about 65.9% on the basis of total nitrogen.

Hydrolysate 3

An amount of 6.25 kg of whey protein (obtained from Meggle GmbH under the trade name Globulal 80) is dispersed in 50 liters of demineralised water at 55° C. The pH of the dispersion is adjusted to 7.5 by the addition of 1.6 liters of 1M $Ca(OH)_2$ and 162 ml of a solution of 1.6M NaOH and 0.4M KOH. The proteins are then hydrolysed using 250 g of Alcalase 2.4L (EC 940459 obtainable from Novo Nordisk Ferment AG). The hydrolysis reaction is continued for 4 hours at 55° C. For the first hour of the reaction, the pH is regulated to 7.6 by the addition of 1.6N NaOH and 0.4N KOH.

An amount of 250 g of Neutrase 0.5L (obtainable from Novo Nordisk Ferment AG) is added and the proteins are further hydrolysed for 4 hours at 50° C. The enzymes are then inactivated by heating the reaction mixture to 90° C. and holding the mixture at this temperature for about 5 minutes. The reaction mixture is then cooled to 55° C.

The pH of the reaction mixture is adjusted to 7.33 by the addition of 1.6N NaOH and 0.4N KOH and the reaction mixture hydrolysed again for 4 hours using 100 g of pancreatin at 55° C. During the reaction, the pH is regulated to 7.5 by the addition of 1M NaOH. The enzymes are then inactivated by heating the reaction mixture to 90° C. and holding the mixture at this temperature for about 5 minutes. The mixture is then cooled to 4° C. The hydrolysed proteins are then dried by lyophilisation and packaged into metal cans.

The hydrolysate has a degree of hydrolysis of about 35% and a non protein nitrogen concentration of about 92.6% on the basis of total nitrogen.

EXAMPLE 2

In order to obtain a nutritional composition intended for specific gastro intestinal maturation in premature mammals, the following mixture is prepared:
  i) 14.5 g/100 g powder total protein content: 10% hydrolysate 2 as prepared in example 1, 40% hydrolysate 3 as prepared in example 1, 50% intact proteins (containing 1 ppm TGFβ2),
  ii) 26 g/100 g powder of fat: 40% medium chain a triglycerides 60% long chain triglycerides
  iii) 53.6 g/100 g powder carbohydrates 65% lactose 35% maltodextrins
  iv) and vitamins, minerals to meet daily requirements.

What is claimed is:

1. A nutritional enteral composition intended for favoring the growth and maturation of non-mature gastrointestinal tracts of young mammals comprising a protein source comprising:

a mixture of whey dietary protein hydrolysates having a degree of hydrolysis in a range of from about 10% to less than 50% by weight, the whey dietary protein hydrolysates in the form of a mixture of different size peptides and free amino acids, the free amino acids being present in an amount of up to about 20% (each calculated as nitrogen ×6.25); and intact proteins comprising bioactive peptides.

2. The composition according to claim 1, wherein the whey dietary protein hydrolysates contain at least about 5% (by weight, of the total protein content calculated as nitrogen ×6.25) of hydrolysate having a degree of hydrolysis of about 40% and at least about 5% of hydrolysates having lesser degree of hydrolysis.

3. The composition according to claim 1 wherein the intact proteins are present in an amount of at least about 5% by weight of the total protein content.

4. The composition according to claim 1 wherein the intact proteins are selected from the group consisting of milk proteins, whey proteins, caseins and TGF-β.

5. The composition according to claim 1 wherein bioactive peptides represent at least about 0.1 to about 4 ng/mg total protein.

6. The composition according to claim 1 which contains the protein source in an amount which provides 5 to 30% of the total caloric content, a source of carbohydrates, which provides 40 to 80% of the total caloric content, a source of lipids, which provides 5 to 55% of the total caloric content, and minerals and vitamins to meet daily requirements.

7. A method of preparing a nutritional enteral composition containing a protein source, whereby the composition is intended for favoring the growth and maturation of non-mature gastro-intestinal tracts of young mammals comprising the step of producing the protein source by blending together of whey dietary protein hydrolysates having a degree of hydrolysis in a range of from about 10% to less than 50% by weight, the whey dietary protein hydrolysates in the form of a mixture of different size peptides and free amino acids, the free amino acids being present in an amount of up to about 20% (each calculated as nitrogen ×6.25) and intact proteins that are at least partially in the form of bioactive peptides.

8. The method according to claim 7 wherein the whey dietary protein hydrolysates comprise at least 5% (by weight, of the total protein content calculated as nitrogen ×6.25) of hydrolysate having a degree of hydrolysis of about 40% and at least 5% of hydrolysates having a lesser degree of hydrolysis.

9. The method according to claim 7 wherein the intact proteins are present in an amount of at least about 5% of the total protein content.

10. The method according to claim 7 wherein the intact proteins are selected from the group consisting of milk proteins, whey proteins, caseins and TGF-β.

11. The method according to claim 7 wherein bioactive peptides represent about 0.1 to about 4 ng/mg total protein.

12. The method according to claim 7 further comprising the step of preparing the nutritional composition so that it contains the protein source in an amount which provides 5 to 30% of the total caloric content, a source of carbohydrates which provides 40 to 80% of the total caloric content, a source of lipids which provides 5 to 55% of the total caloric content, minerals and vitamins to meet daily requirements.

13. A method for providing nutrition to young mammals having non-mature gastro-intestinal tracts, comprising the step of administering to the young mammal a composition which contains as a protein source a mixture of whey dietary protein hydrolysates having a degree of hydrolysis in a range of from about 10% to less than 50% by weight, the whey dietary protein hydrolysates in the form of a mixture of different size peptides and free amino acids, the free amino acids being present in an amount of up to about 20% (each calculated as nitrogen ×6.25) and intact proteins that are at least partly in the form of bioactive peptides.

14. The method according to claim 13 wherein the whey dietary protein hydrolysates contain at least about 5% (by weight, of the total protein content calculated as nitrogen ×6.25) of hydrolysate having a degree of hydrolysis of about 40 and at least about 5% of hydrolysates having a lesser degree of hydrolysis.

15. The method according to claim 13 wherein the intact proteins are present in an amount of at least about 5% by weight of the total protein content.

16. The method according to claim 13 wherein the intact proteins are selected from the group consisting of milk proteins, whey proteins, caseins and TGF-β.

17. The method according to claim 13 wherein the bioactive peptides represent at least about 0.1 to about 4 ng/mg total protein.

18. The method according to claim 14 wherein the composition comprises the protein source in an amount which provides 5 to 30% of the total caloric content, a source of carbohydrates which provides 40 to 80% of the total caloric content, a source of lipids which provides 5 to 55% of the total caloric content and minerals and vitamins to meet daily requirements.

19. A method for promoting the growth and maturation of non-mature gastrointestinal tracts of young mammals, comprising the steps of administering to the young mammal a composition which contains as a protein source a mixture of whey dietary protein hydrolysates having a degree of hydrolysis in a range of from about 10% to less than 50% by weight, the whey dietary protein hydrolysates in the form of a mixture of different size peptides and free amino acids, the free amino acids being present in an amount of up to about 20% (each calculated as nitrogen ×6.25) and intact proteins that are at least partly in the form of bioactive peptides.

20. The method according to claim 19 wherein the whey dietary protein hydrolysates contain at least about 5% (by weight, of the total protein content calculated as Nitrogen ×6.25) of hydrolysate having a degree of hydrolysis of about 40 and at least about 5% of hydrolysates having a lesser degree of hydrolysis.

21. The method according to claim 19 wherein the intact proteins are present in an amount of at least about 5% by weight of the total protein content.

22. The method according to claim 19 wherein the intact proteins are selected from the groups consisting of milk proteins, whey proteins, caseins and TGF-β.

23. The method according to claim 19 wherein bioactive peptides represent at least about 0.1 to about 4 ng/mg total protein.

24. The method according to claim 19 wherein the composition contains the protein source in an amount which provides 5 to 30% of the total caloric content, a source of carbohydrates which provides 40 to 80% of the total caloric content, a source of lipids which provides 5 to 55% of the total caloric content and minerals and vitamins to meet daily requirements.

* * * * *